United States Patent [19]

Warchol et al.

[11] Patent Number: 4,731,732

[45] Date of Patent: Mar. 15, 1988

[54] METHOD AND APPARATUS FOR DETERMINING SOLUBLE GAS CONTENT

[75] Inventors: Mark F. A. Warchol, New Kensington; Ronald C. Wojnar, Upper Burrell Township, West Moreland County, both, Pa.

[73] Assignee: Aluminum Company of America, Pittsburgh, Pa.

[21] Appl. No.: 763,290

[22] Filed: Aug. 7, 1985

[51] Int. Cl.$^4$ .......................... G01N 7/14; G01K 1/12
[52] U.S. Cl. .................................. 364/510; 364/472; 364/497; 73/19
[58] Field of Search ............... 364/510, 472, 477, 497; 73/19

[56] References Cited

U.S. PATENT DOCUMENTS

| | | | |
|---|---|---|---|
| 2,861,450 | 11/1958 | Ransley | 73/19 |
| 3,517,543 | 6/1970 | Gasser. | |
| 3,561,743 | 2/1971 | Schroeder | 364/477 |
| 3,820,380 | 6/1974 | Miller et al. | 73/19 |
| 3,949,590 | 4/1976 | Boillot | 73/19 |
| 4,133,036 | 7/1979 | Watson | 364/477 |
| 4,142,399 | 3/1979 | Sato et al. | 73/19 |
| 4,179,918 | 12/1979 | Van Strien | 73/19 |
| 4,239,532 | 12/1980 | Allersama et al. | 73/19 |
| 4,305,906 | 12/1981 | Mikasa et al. | 73/19 |
| 4,447,301 | 5/1984 | Shen | 364/497 |
| 4,454,748 | 6/1984 | Terai et al. | 73/19 |
| 4,550,590 | 11/1985 | Kessen | 73/19 |

Primary Examiner—Parshotam S. Lall
Attorney, Agent, or Firm—Elroy Strickland

[57] ABSTRACT

A method of determining the gas content of a body or flow of molten metal of a known alloy. The method includes the steps of providing a carrier gas and directing the same into the molten metal. The carrier gas creates in the molten metal free surfaces such that molecules of the gas content migrate to the free surfaces and accumulate in the carrier gas. The method next determines the occurrence of equilibrium between the carrier gas and the gas content in the molten metal, the magnitude of equilibrium pressure, and the temperature of the molten metal. Signals are developed representing respectively the equilibrium pressure and temperature, which signals are directed to a computing device. Information is also directed to the computing device that represents the solubility of the gas content in the alloy of the molten metal under test. The computing device calculates the gas content of the molten metal from the equilibrium pressure, molten metal temperature and solubility information to provide a direct and accurate readout of the gas content.

2 Claims, 4 Drawing Figures

METHOD AND APPARATUS FOR DETERMINING SOLUBLE GAS CONTENT

BACKGROUND OF THE INVENTION

The present invention is related generally to a method of determining the amount of soluble gas contained in a body of molten metal and particularly to a method that provides a direct and accurate measurement of such gas content.

Hydrogen is pressure the most important gas found in aluminum and aluminum alloys. It dissolves in the metal in the atomic state and at any free surface tends to escape to set up equilibrium in accordance with the relation: Concentration of hydrogen in solution is equal to a constant times partial pressure, where partial pressure is the equilibrium pressure of the molecular hydrogen at the free surface of molten metal. If the solubility "SO" of hydrogen at a given pressure (e.g., 760 mm of mercury) is known, then a given gas content "G" will give rise to an internal or equilibrium pressure Pi such that:

$$G = SO \, Pi/760 \tag{1}$$

An instrument for measuring equilibrium pressure is disclosed in U.S. Pat. No. 2,861,450 to Ransley. To convert the measurement of equilibrium pressure in the Ransley instrument to a measurement of gas content in terms of cubic centimeters per 100 grams of metal, it is only necessary to know the solubility of hydrogen in the alloy of the metal being measured. The solubilities of the important alloys have been determined, and the solubility increases with increases in the temperature of the molten alloy.

The Ransley device employs active collection of hydrogen from the melt by means of a neutral carrier gas. If a carrier gas, such as nitrogen, is passed through the molten metal, hydrogen diffuses out of the melt into tiny bubbles created in the melt by the flow of nitrogen. After a period of time and repeated circulation of the nitrogen through the molten metal the two gases obtain equilibrium.

The hydrogen collected in the carrier gas is determined, in the Ransley patent, by a hot wire catharometer, the catharometer being comprised of two identical cell structures, each containing a fine platinum wire as the sensing element. One of the two cells, i.e., the measuring cell, is serially connected in the flow of the carrier gas while the other cell is open to the atmosphere. The two cells are electrically connected in a simple bridge circuit, with a small electrical potential (voltage) being applied across the bridge and the cells to heat the platinum elements. The hydrogen gas collected by the carrier gas is directed to the measuring cell. The hydrogen diffuses in the cell and cools the wire filament. This cooling increases the electrical resistance of the platinum and this unbalances the bridge circuit; a meter connected across the bridge circuit reads the out-of-balance condition; this out-of-balance condition is the measurement of equilibrium pressure.

Personnel using the instrument of the Ransley patent must now convert the meter reading to a set of values that determines the actual hydrogen content of the molten metal in terms of cc of H/100 grams of pure aluminum. The conversion is made from charts of conversion factors, including temperature, that function as multipliers to adjust the hydrogen value from that of pure aluminum to the appropriate alloy of aluminum. As explained in detail below, the visual reading of a meter by personnel working in foundries, and then converting and correcting by hand subjects such readings to errors. What is therefore needed is a method by which direct, repeatedly accurate readouts of gas content is obtained from an instrument that measures equilibrium pressure and makes the appropriate calculations automatically.

BRIEF SUMMARY OF THE INVENTION

The present invention is directed to a method by which direct readings of equilibrium pressure are obtained without the use of charts. The method includes the use of a computing device that measures directly the unbalance of a bridge circuit occurring with the accumulation of hydrogen in an inert carrier gas directed to a measuring cell in a bridge circuit. The temperature of the molten metal is measured and also directed to the computing device. In addition, the computing device is informed of the alloy of the molten metal by a workman, which information represents the solubility of hydrogen in the molten metal of the alloy. From the unbalanced value of the bridge and from the solubility and temperature information directed to the computing device, the device calculates precisely and outputs directly the amount of hydrogen in the batch or flow of molten metal under test.

BRIEF DESCRIPTION OF THE DRAWINGS

The advantages and objectives of the invention will be best understood from consideration of the following detailed description and the accompanying drawings, in which.

AN EMBODIMENT OF THE INVENTION

Figure 1:
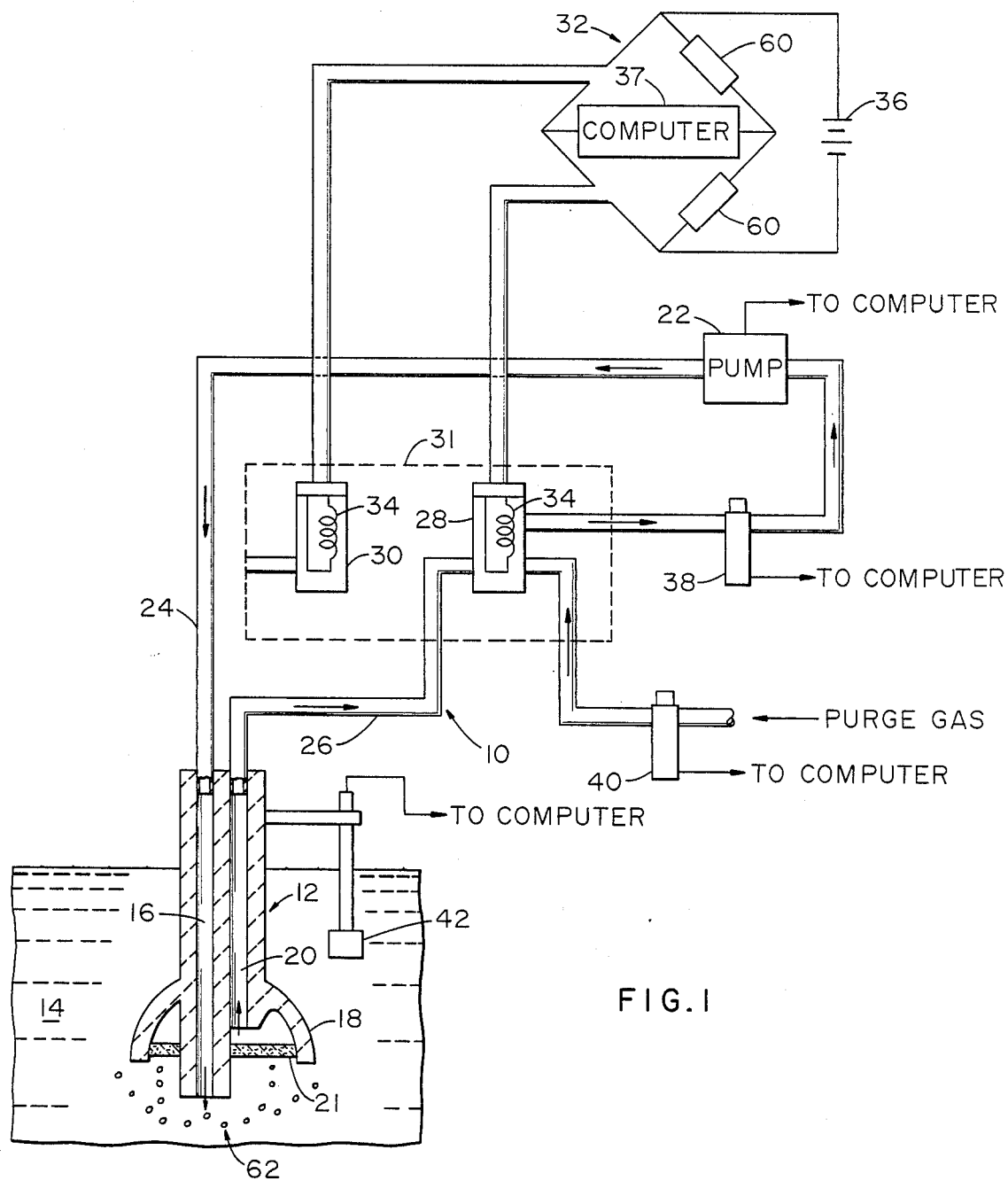
FIG. 1 is a diagrammatic representation of the system for measuring the equilibrium pressure between the gas content of a static body or moving flow of molten metal and an inert carrier gas.

Referring now to FIG. 1 of the drawings, a system 10 is depicted in which a heat resistant ceramic probe 12 is located in a body or flow of molten metal 14. The structure of the probe is such that a capillary tube portion 16 extends below a collector cup or bell 18, with a second capillary tube portion 20 terminating above the lower edge of the cup and above a ceramic filter 21 located across the lower end of the cup.

Tube portion 16 of probe 12 is connected to a suitable, low pressure pump 22 by a capillary, needle-type tube 24. The material of tube 24 is preferably steel. A similar capillary tube 26 connects ceramic tube 20 to a cell 28 that measures equilibrium pressure between two gases in a manner explained below. A companion comparison cell 30 is shown in FIG. 1 connected in fluid communication with the atmosphere. Both cells are preferably physically part of and housed in a brass block 31, indicated in dash outline in FIG. 1.

Cells 28 and 30 are each comprised of identical fine, platinum wire elements 34, the two elements being connected in electrical series and providing two legs of a bridge circuit 32. The wire elements are heated by a small dc current provided by a low voltage battery 36 electrically connected across the bridge circuit.

Battery 36 also powers a computing device 37 electrically connected across the bridge circuit. The computing device is preferably a commercially available CMOS microcomputer having low power requirements, for purposes of conserving the charge of battery 36. The computing device is also programmable in a manner explained hereinafter.

Measuring cell 28 is connected in fluid communication with pump 22 via a solenoid valve means 38, and with a solenoid valve 40 that is employed to purge cell 28 and probe 12 in a manner described below. Valve 40 is connected to a supply of purge gas, as shown schematically in FIG. 1, which gas is an inert gas, such as a dry grade nitrogen or argon.

Still referring to FIG. 1 of the drawings, a device 42, a thermocouple, for example, is provided for measuring the temperature of molten body or flow 14. The device is preferably mounted on probe 12 so that the temperature sensor and probe can be simultaneously lowered over and into the liquid metal.

The operation of system 10, as thus far described, is as follows. Preferably, computing device 37 has no on-off power switch. Rather, 37 is always powered, but powered in a sleep or hibernate mode that utilizes minimum power from battery 36. The computing device remains in an inactive condition until activated by either pushing a designated button on a keypad 46 (FIG. 2) interfaced at 48 with the central processing unit (CPU) 50 of computer 37, or by positioning probe 12 in close proximity to, but not in the body of molten metal; to prevent thermal shock to the probe, the probe is preheated before being disposed in molten metal. The computing device is turned on by the heat radiating from the metal and reaching sensor 42; 42 outputs a signal to the computer via an amplifier 52 to turn on the computer when the temperature of the sensor reaches say 100° C., for example.

Figure 2:
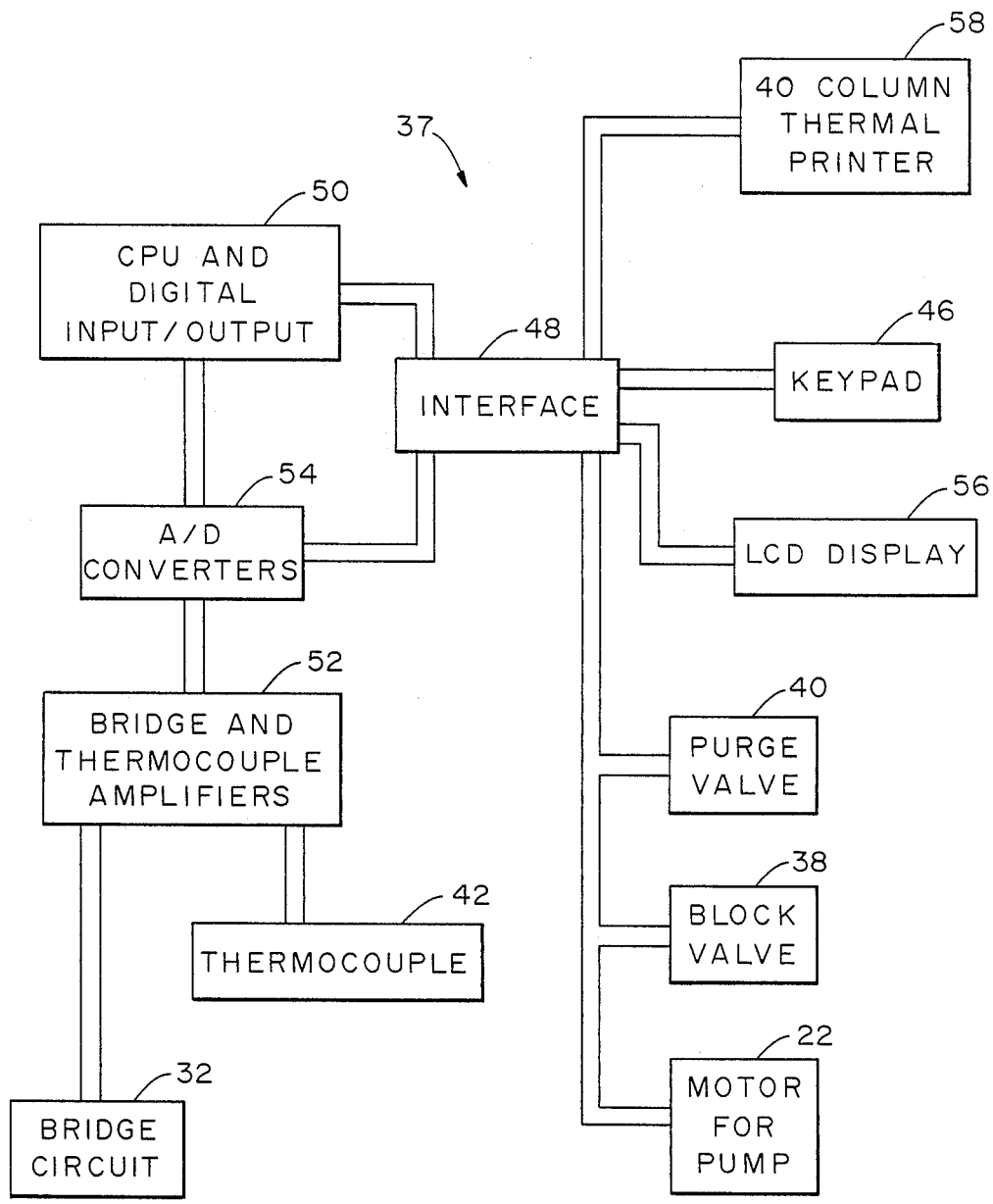
FIG. 2 is a schematic diagram of the automatic functions of the system of FIG. 1.

Computer 37 is interfaced at 48 to receive signals from bridge circuit 32 and temperature sensor 42 via amplifiers 52 and analogue-to-digital converters 54. Similarly, an LCD (liquid crystal display) device 56 is shown, and is interfaced at 48 with the CPU and program units of computer 37. A 2K non-volatile memory (not shown) is suitable for this purpose, and appropriate electrical connections and data buses are shown in FIG. 2 connecting the respective components together.

After activation, the computer asks a workman to enter a number representing the alloy of the metal under test, and the computer can be programmed to ask for verification of the number. Such a number (correction factor) can be taken, for example, from one of the following tables for wrought and casting mold aluminum alloys.

TABLE I

| CORRECTION FACTORS FOR WROUGHT ALUMINUM ALLOYS | |
|---|---|
| Alloy | Correction Factor |
| 1100 | 1 |
| 2014 | 0.73 |
| 2017 | 0.75 |
| 2024 | 0.79 |
| 2219 | 0.63 |

TABLE I-continued

| CORRECTION FACTORS FOR WROUGHT ALUMINUM ALLOYS | |
|---|---|
| Alloy | Correction Factor |
| 3003 | 1 |
| 3004 | 1.04 |
| 3005 | 1.01 |
| 4543 | 0.85 |
| X5015 | 1.03 |
| 5050 | 1.06 |
| 5052 | 1.10 |
| 5053 | 1.14 |
| 5056 | 1.20 |
| 5082 | 1.18 |
| 5086 | 1.16 |
| 5154 | 1.14 |
| 5457 | 1.03 |
| 5657 | 1.03 |
| 6061 | 1.01 |
| 6062 | 1.01 |
| 6063 | 1.03 |
| 6151 | 1.02 |
| 7001 | 1 |
| 7075 | 1 |
| 7079 | 1.09 |
| 7178 | 0.98 |

TABLE II

| CORRECTION FACTORS FOR SAND AND PERMANENT MOLD CASTING ALLOYS | |
|---|---|
| Alloy | Correction Factor |
| X250 | 1.31 |
| 333 | 0.54 |
| 344 | 0.81 |
| 355 | 0.81 |
| C355 | 0.81 |
| 356 | 0.83 |
| A356 | 0.83 |
| F132 | 0.62 |
| 214 | 1.15 |
| A214 | 1.15 |
| F214 | 1.14 |
| 220 | 1.4 |
| 319 | 0.61 |

In using the instrument of the above Ransley patent, a workman reads the meter in the bridge circuit, finds this reading on the ordinate of one of the charts (FIG. 3 or 4), notes the temperature of the molten metal and then reads the percent of hydrogen from the abscissa of the chart. The percent of hydrogen read, however, from the chart was (and is) in terms of pure aluminum. The workman then had to convert this reading for the alloy of the melt under test by using the correction factor of the alloy, such as found in one of the above tables. As can be appreciated, such a process is cumbersome and subject to error.

Computer 37 now waits for probe 12 to reach and maintain a predetermined preheat temperature, say 125° C. for about ten minutes. As noted above, the probe is heated before it is disposed in the hot metal to prevent damage to the probe. If probe 12 is already at or above this temperature, as a result of a recent insertion in the molten metal, for example, the wait period can be shortened or eliminated by pressing an appropriate key on keypad 46. The program of the computer, however, will not permit such an override if probe 12 is not at or above the preheat temperature.

After completion of the preheat cycle, the program of computer 37 asks the workman if he wishes to insert the probe into the hot metal. If the workman wishes to insert the probe, he confirms this by (again) pushing an appropriate button on keypad 46. Upon such confirmation, the computer orders purging of the probe and measuring cell 28 and instructs (via display 56) the workman to insert the probe into the molten metal.

A purge cycle is next effected automatically by the opening of solenoid valve 40 on orders from the computer. The opening of valve 40 allows an inert purge gas, which is under pressure, to flow through cell 38 and through tube portion 20 of probe 12. The purge gas is also directed through tube portion 16 of probe 12, the flow to tube portion 16 being through the valve of solenoid 38 and pump 22. The valve of 38 is presently open and remains open until ordered closed by the computer. The flow of gas from 40 purges the system (except for cell 30) of air (and thus any residual hydrogen) and clears away any films of aluminum oxide located on cup 18 and filter 21 of the probe.

While the system is purged with inert gas, the test for the percentage of hydrogen in molten metal 14 begins by zeroing the measurement system. This system includes two fixed resistors 60 of bridge circuit 32. The electrical resistances of 60 are substantially equal to the electrical resistances of the wire filaments 34 in cells 28 and 30, filaments 34 providing the other half of the bridge. As noted earlier, cell 30 is opened to the atmosphere, which atmosphere contains a relatively constant amount of hydrogen gas. This hydrogen constant is balanced against the pure inert gas in cell 28 to obtain a "zero" value indicative of such balance. This value is received and stored in unit 52 (FIG. 2) of computer 37 (connected directly across the bridge) for future calculation of hydrogen content.

Computer 37 now orders the closing of the valve in solenoid 40 to end the purging process and capture the inert gas in the system. The system, i.e., the capillary tubes 24 and 26, and those of probe 12, along with cell 28 and pump 22, are now filled with the inert purge gas. The computer also now starts pump 22, which pumps the inert gas into the body or flow of molten metal 14. The valve of solenoid 38 blocks reverse flow of the inert gas through the system, such that the flow is in the direction of the arrows depicted in the tubing shown in FIG. 1.

The inert, i.e. carrier, gas enters the molten metal from the end of tube 16, presently immersed in the metal, as shown in FIG. 1. The flow of the carrier gas into molten metal creates a stream of bubbles 62 therein, some of which are captured by the collector bell 18 of the probe. From the bell the carrier gas is returned to measuring cell 28, via tube 26, and to pump 22, the pump continuing the cycle of directing carrier gas to the molten metal and returning the gas to cell 28.

The bubbles 62 formed in molten metal 14 provide free surfaces in the metal to which molecules of the hydrogen gas dissolved in the metal tend to escape. As the bubbles are formed and the carrier gas is circulated into and from the molten metal, hydrogen gradually transfers to the carrier gas which carries off hydrogen to measuring cell 28. The transfer of hydrogen to the carrier gas continues until the carrier gas reaches equilibrium with the percent of hydrogen gas in the molten metal, i.e., in accordance with formula 1 discussed above. As the transfer takes place, the heated filament 34 of cell 28 (the filament being heated by its resistance to the flow of current provided by battery 36) is gradually cooled by the presence of hydrogen in the cell, i.e., the inert carrier gas, such as nitrogen or argon, which is a poor conductor of heat in comparison to hydrogen.

The gradual cooling of the filament in 28 gradually lowers its electrical resistance, which, in turn causes gradual unbalancing of bridge 32. When the unbalancing process stops, equilibrium has been attained between the carrier gas and the gas content of molten metal 14. Computer 37 continuously monitors this process; when the process ceases, the computer notes this and stops the flow of gas by stopping operation of pump 22.

Computer 37 now reads the degree of the unbalance of bridge circuit 32 and substracts the zero value obtained earlier from this reading to provide a value that is employed in the CPU 50 of the computer to calculate directly the percent (based on cc of H/100 grams of metal) of hydrogen dissolved in the molten metal. This calculation also utilizes the temperature of the molten metal as read and directed to the CPU by sensor 42, (noting again that the solubility of hydrogen is affected by temperature), and the solubility of hydrogen in the particular alloy of the metal, which information has been given to the computer by the workman in the manner discussed above. The CPU of 37 processes this information, to provide instantly a direct readout of the percent of hydrogen content in the alloy of molten metal 14. As indicated in FIG. 2 of the drawings, the readout can be in the form of liquid crystal display 56 and a hard copy printout 58. The printout, in addition, can show the temperature and alloy correction factors on which the calculation of percent hydrogen is based.

Figure 3:
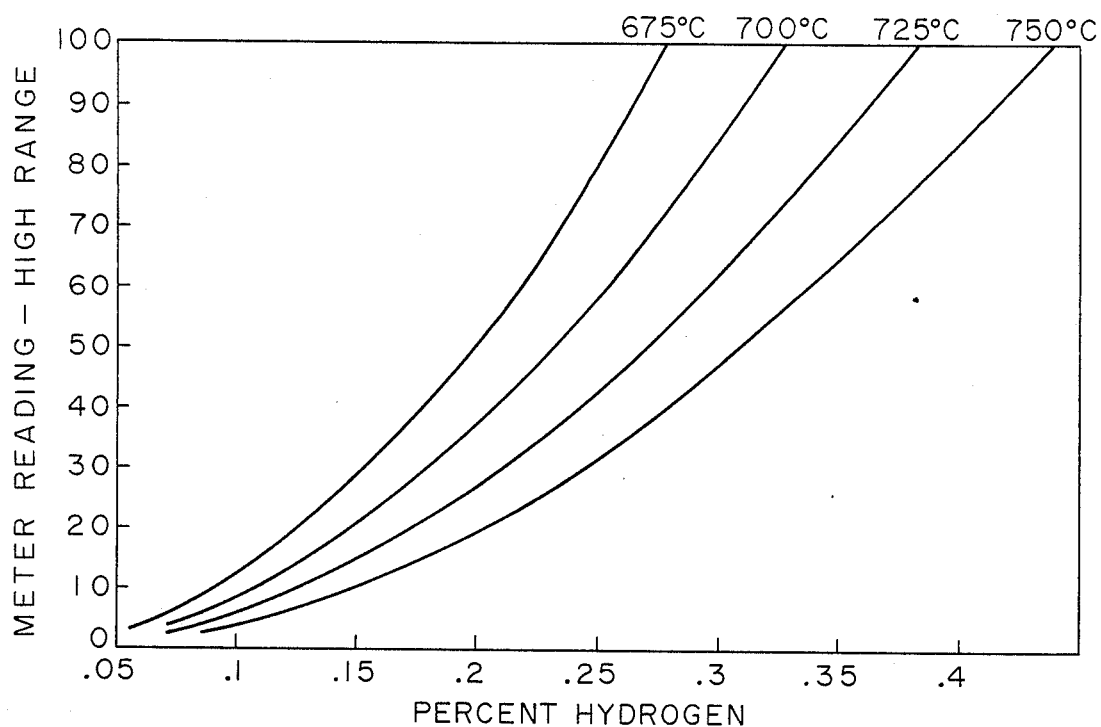
FIG. 3 is a chart employed in the prior art to determine the amount of gas content in a batch or flow of molten metal in which alloy correction factors lie in a "high range.
Figure 4:
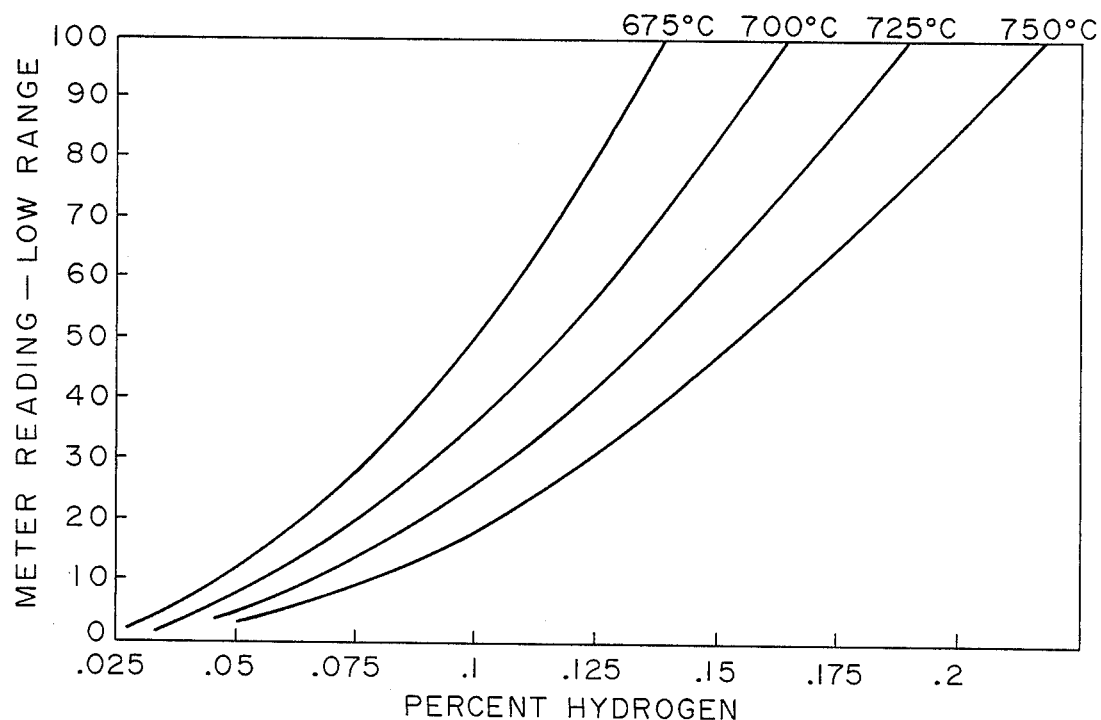
" and FIG. 4 is a prior art chart similar to that of FIG. 3 except that the alloy correction factors are in a "low range."

As seen in the charts of FIGS. 3 and 4 isotherms of the hydrogen content are charted every 25° C. However, temperatures of the molten metal are usually measured within 1° C. Thus, two persons with the same input data (alloy correction factor, temperature reading and a meter reading of bridge circuit unbalance) can arrive at two different hydrogen contents. This is particularly a problem on the foundry and production floor if non-technical people are required to do the measuring, chart reading and arithmetic involved in correcting for the alloy being tested. The method of the present invention, however, provides consistent, reproducible, accurate results. The computer provides as much as four place readings, a result impossible with the method of the prior art.

While the invention has been described in terms of preferred embodiments, the claims appended hereto are intended to encompass all embodiments which fall within the spirit of the invention.

What is claimed is:

1. A method of determining the amount of gas content dissolved in molten metal of a known alloy and temperature, the gas content having a known solubility in the known alloy, the method comprising the steps of:
   (a) providing a body or flow of said metal,
   (b) providing a flow of carrier gas,
   (c) directing the carrier gas into and circulating the same in the molten metal to create therein free surfaces in the metal and thereby accumulate free molecules of the gas content dissolved in the metal in the flow of the carrier gas such that equilibrium pressure of the carrier and content gases occurs at a measurable magnitude,
   (d) determining the occurrence and magnitude of the equilibrium pressure,
   (e) measuring the temperature of the molten metal,
   (f) developing and directing electrical signals representing respectively said temperature and equilibrium pressure to a computing device, (g) informing the computing device of a number that represents the solubility of the gas content in the alloy of the molten metal, and (h) said computing device thereafter calculating the gas content of said body of molten metal from said signals, solubility number and temperature measurement to provide a direct and accurate reading of said gas content.

2. The combination comprising:

(a) a heat resistant probe for directing a flow of carrier gas into and circulating the same in a body of molten metal of a known alloy and temperature in a process for determining the amount of soluble gas contained in the molten metal, said flow of carrier gas accumulating molecules of the soluble gas contained in said metal until equilibrium occurs at a measurable pressure, (b) means for sensing the pressure of said equilibrium and for developing electrical signals representative of said pressure, (c) means insertable into said molten metal for sensing the temperature thereof and for developing electrical signals representative of said temperature, (d) means for directing said signals to a computing device programmed to:

(1) assume an inactive operational mode until activated, (2) become activated when the probe is heated to a certain preheat temperature before it is lowered into the molten metal, (3) ask for a number representing the degree in which the gas is soluble in the alloy of the molten metal, (4) wait for the temperature of the probe to attain the preheat temperature, (5) order purging of the probe and means for sensing equilibrium pressure with the carrier gas, (6) ask for insertion of the probe into the molten metal, and thereafter, (7) stop the purging process; and (8) circulate the carrier gas through the probe and into the molten metal, and through the means for sensing equilibrium pressure, said carrier gas accumulating free molecules of the gas contained in the molten metal, said computing device, in addition, being:

(1) programmed to accurately compute the amount of the gas contained in the molten metal from the signals of equilibrium pressure and temperature of the molten metal, and from the solubility number, and (2) provide a direct readout of said computation.

* * * * *